(12) United States Patent
Orlov et al.

(10) Patent No.: US 6,699,676 B1
(45) Date of Patent: Mar. 2, 2004

(54) USES OF OUABAIN AND OUABAIN-LIKE MOLECULES IN APOPTOSIS RELATED PATHOLOGIES

(75) Inventors: Sergei N. Orlov, Montreal (CA); Pavel Hamet, Ville Mont-Royal (CA); Johanne Tremblay, Ville Mont-Royal (CA)

(73) Assignee: Corporation du Centre de Recherche du Centre, Hospitalier du L'Universite de Montreal, Montreal (CA)

( * ) Notice: Subject to any disclaimer, the term of this patent is extended or adjusted under 35 U.S.C. 154(b) by 25 days.

(21) Appl. No.: 09/586,097

(22) Filed: Jun. 2, 2000

(30) Foreign Application Priority Data

Jun. 3, 1999 (CA) ............................................ 2273699

(51) Int. Cl.[7] ...................... G01N 33/567; A01N 45/00; A01N 43/42; A61K 49/00
(52) U.S. Cl. .......................... 435/7.21; 514/26; 514/280; 514/284; 424/9.1
(58) Field of Search .......................... 514/26, 280, 284; 424/9.1; 435/7.21

(56) References Cited

U.S. PATENT DOCUMENTS

| | | | | |
|---|---|---|---|---|
| 3,843,628 | A | 10/1974 | Minato | 260/210.5 |
| 4,020,159 | A | 4/1977 | Herrmann | 424/180 |
| 4,175,078 | A | 11/1979 | Makarevich et al. | 260/239.57 |
| 5,153,178 | A | 10/1992 | Maroko | 514/26 |
| 5,602,105 | A | 2/1997 | Karsanov et al. | 514/26 |
| 5,695,944 | A | * 12/1997 | Croce et al. | 435/7.21 |

FOREIGN PATENT DOCUMENTS

WO    WO 9405305    3/1994

OTHER PUBLICATIONS

Olej et al. (Bioscience Reports (1998) 18(1): 1–7).*
Xiao et al. (J. of Neuroscience (2002) 22(4): 1350–1362).*
Hardman et al. (The Pharmacological Basis of Therapuetics (1996) pp. 810–813).*
Djuricic et al. (Biochemical Society Transactions (1996) 24(4) 612S).*
Pchejetski et al. (Biochemical and Biophysical research Communications (2003) 301: 735–744.*
Bogdan Djuricic et al., Inhibiting of (NA,K)ATPASE in Thymocytes Reduces Apoptosis Induced by Microtubule–Disrupting Agents, vol. 24, No. 4, 1996, p. 612S, XP–001004750.
Bogdan Djuricic et al., "Apoptocic Thymocytes Change Appearance if Ionic Pump is Inhibited", vol. 4, No. 14, 1998, pp. 815–816, XP–002174776/
Foey A.D. et al., "Dysfunctional NA/K–ATPASE Activity in Rheumatoid Synovial Lining Cells Results in a Defect in FAS–Mediated Apoptosis", vol. 39, No. 9, 1996, pp. S132, XP–001004746.

Goodman–Gilman A. "The pharmacological basis of therapeutics" 1985, Macmillan Publ. Company, 7th Ed.,.
Francis, J. Haddy, "Potassium Effects on Contraction in Arterial Smooth Muscle Mediated by NA+, K+–ATPASE", vol. 42, No. 2, 1983, pp. 239–245, XP–001004735.
Chemical Abstracts Service, Columbus, Ohio, SU, AN=1997;400150, XP–002174778.
Jutta Urenjak et al., "Pharmacological Modulation of Voltage–Gated Na+ Channels: A Rational and Effective Strategy Against Ischemic Brain Damage", vol. 48, No. 1, 1996, pp. 21–67, XP–001004731.
Sergei N. Orlov et al., "Inversion of the Intracellular NA+/K+ Ratio Blocks Apoptosis in Vascular Smooth Muscle at a Site Upstream of Caspase–3", Journal of Biological Chemistry, American Society of Biiological Chemists, Baltimore, MD, US, vol. 274, No. 23, 1999, pp. 16545–16552, XP–000993597.
Isaev N.K. et al., "Inhibition of NA+, K+–ATPASE Activity in Cultured Rat Cerebellar Granule Cells Prevent the Onset of Apoptosis Induced by Low Potassium", Neuroscience Letters, Limerick, IE, vol. 283, No. 1, 2000, pp. 41–44, XP–001004641.
Database Medline, STN AN=2000094461, XP–002174779 & Parmley: "Surviving heart failure: Robert L. Frye lecture", Mayo Clin. Proc., vol. 75, No. 1, 2000, pp. 111–118.
Sergei N. Orlov et al., "Inversion of the Intracellular NA+/K+ Ratio Blocks Apoptosis in Vascular Smooth Muscle Cells by Induction of RNA Synthesis", Hypertension, vol. 35, No. 5, 2000, pp. 1062–1068, XP–001004747.

(List continued on next page.)

Primary Examiner—Kenneth R. Horlick
Assistant Examiner—Alexander H. Spiegler
(74) Attorney, Agent, or Firm—Myers Bigel Sibley & Sajovec, PA

(57) ABSTRACT

Longterm elevation of the intracellular $Na^+/K^+$ ratio inhibits macromolecule synthesis and proliferation in the majority of cell types studied so far, including vascular smooth muscle cells (VSMC). We report here that inhibition of the $Na^+,K^+$ pump in VSMC by ouabain or 1 hour preincubation in $K^+$-depleted medium attenuated apoptosis triggered by serum withdrawal, staurosporine or okadaic acid. In the absence of ouabain, both DNA degradation and caspase-3 activation in VSMC undergoing apoptosis were insensitive to modification of the extracellular $Na^+/K^+$ ratio as well as to hyperosmotic cell shrinkage. In contrast, protection of VSMC from apoptosis by ouabain was abolished under equimolar substitution of $Na^+_o$ with $K^+_o$, showing that the anti apoptotic action of $Na^+,K^+$ pump inhibition was caused by inversion of the intracellular $Na^+/K^+$ ratio. Unlike VSMC, the same level of increment of the $[Na^+]_i/[K^+]_i$ ratio caused by 2 hours preincubation of Jurkat cells with ouabain did not affect chromatin cleavage and caspase-3 activity triggered by treatment with Fas ligand, staurosporine or hyperosmotic shrinkage. Thus, our results show for the first time that similarly to cell proliferation, maintenance of a physiologically low intracellular $Na^+/K^+$ ratio is required for progression of VSMC apoptosis.

11 Claims, 7 Drawing Sheets-

OTHER PUBLICATIONS

Robert J. Mark et al., "Amyloid β–Peptide Impairs Ion–Motive ATPase Activities: Evidence for a Role in Loss of Neuronal CA2+ Homeostasis and Cell Death", Journal of neuruscience, vol. 15, No. 9, 1995, pp. 6239–6249, XP–001004822.

Marklund L. et al., "K+–Efflux Modulation of Cisplatin–Induced Apoptosis and Cytotoxicity to Cultured Mesothelioma Cells", Investigative Ophthalmology & Visual Science, Association for Research in Vision and, US, vol. 38, No. 4, 1999, p. S109, XP–001006189.

Orlov SN, Thorin–Trescases N, Kotelevtsev SV, Tremblay J, Hamet P: Inversion of the Intracellular Na$^+$/K$^+$ ratio blocks apoptosis In Vascular smooth muscle at a site upstream of caspase–3. *J. Biol. Chem.* 1999, 274:16545–16552.

Orlov SN, Taurin S, Thorin–Trescases N, Dulin NO, Tremblay J, Hamet P: Invasion of the Intracellular Na$^+$/K$^+$ ratio blocks apoptosis in vascular smooth muscle cells by induction of RNA synthesis. *Hypertension* 2000, 35:1062–1068.

Orlov SN, Li J–M, Tremblay, J, Hamet P: Genes of Intracellular calcium metabolism and blood pressure control in primary hypertension. *Seminar in Nephrology* 1995, 15:569–592.

Orlov SN, Adragna N, Adarichev VA, Hamet P: Genetic and biochemical determinants of abnormal monovalent ion transport in primary hypertension. *Am. J. Physiol.* 1999, 276:C511–C536.

Akera T, Ny YC: Digitals sensitivity of Na,K–ATPase, myocytes and heart. *Life Sci.* 1991, 48:97–106.

Lubin M: Intracellular potassium and macromolecular synthesis in mammalian cells. *Nature* 1967, 213:451–453.

Szamel M, Reshkin SJ: Inhibition of lymphocyte activation by ouabain. Interference with the early activation of membrane phospholipid metabolism. *Biochim.Biophys.Acta* 1981, 647:297–301.

Murata Y, Matsuda T, Tamada K, Hosoi R, Asano S, Takuma K, Tanaka K, Baba A: Quabain–Induced cell proliferation in cultured rat astrocytes. *Jpn. J. Pharmacol.* 1996, 72:347–353.

Kaplowitz PB, Moscona AA: Stimulation of DNA synthesis by ouabain and concanavalin A in cultures of embryonic neuronal retina cells. *Cell Differ.* 1976, 5:109–119.

Bonnard C, Lechner JF, gerwin BI, Fujiki H, Harris CC: Effects of palytoxin or ouabain on growth and aquamous differentiation of human bronchial epithelial cells in vitro. *Carcinogenesis* 1988, 9:2245–2249.

Lubin M, Ennis HL: On the role of intracellular potassium in protein synthesis. *Biochim.Biophys.Acta* 1964, 80:614–631.

Snank BB, Smith NE: Regulation of cellular growth and sodium pump activity. *J.Cell.Physiol.* 1976, 87:377–388.

Frantz CN, Stiles CD, Pledger WJ, Scher CD: Effect of ouabain on growth regulation by serum components in Balb/c–3T3 cells: Inhibition of entry into S phase by decreased protein synthesis. *J.Cell.Physiol.* 1980, 105:439–448.

Leong, SL, Ma WC, Chen MC, Lau YT: Inhibition of protein synthesis by reduced K+ in cultured endothelial cells. *Clin. J.Physiol.* 1997, 30:1430148, Abstract.

Huang L, Li H, Xie Z: Ouabain–Induced hypertrophy in cultured cardiac myocytes is accompanied by changes in expression of several late response genes. *J.Mol.Cell.Cardiol.* 1997, 29:429–437.

OrlovSN, Taurin S, Tremblay J, Hamet P: Both apoptosis and proliferation of smooth muscle cells are effected by Na+,K+ pump inhibition: possible implication in vascular remodeling. *J. Hypertens.* 2000, submitted.

Olej B, dos Santos NF, Leal L, Rumjanek VM: Ouabain induces apoptosis in PHA–activated lymphocytes. *Biosci.Rep.* 1998, 18:1–7.

Lubin M: Control of growth by intracellular potassium and sodium concentrations is relaxed in transformed cells, *Biochem.Biophys.Res.Commun.* 1980, 97;1060–1067.

Falciola J, Volet B, Anner MRM, Moosmayaer M, Locotte D, Annwe BM: Role of cell membrane of Na,K–ATPase for survival of human lymphocytes in vitro. *Biosci.Rep.* 1994, 14:189–204.

Senatorov, W, Stys PK, Hu B: Regulation of Na$^+$, K$^+$–ATPase by persistent sodium accumulation in adult rat thalamic neurons. *J. Physiol.* 2000, 525:343–353.

Warny M, Kelly CP: Monocytic cell necrosis in mediated by potassium depletion and caspase–like proteases. *Am.J. Physiol.* 1999, 276:C717–C724.

Verheye–Dua F, Bohm L: Na$^+$, K$^+$–ATPase Inhibitor, ouabain, accentuates irradiation damage in human tumor cell lines. *Radiat.Oncol.Invest*. 1998, 6:109–119.

Matsumori A, Ono K, Nishio R, Igata H, Shioi T, Matsui S, Furukawa Y, Iwasaki A, Nose Y, Sasayama S: Modulation of cytokine production and protection against lethal endotoxemia by the cardiac glycoside ouabain. *Circulation* 1997, 96:1501–1506.

Isaev NK, Stelmshook EV, Halle A, Harms C, Lautenschlager M Weih M, Dirnagl U, Victorov IV, Zorov DB: Inhibition of Na+,K+–ATPase activity in cultured cerebellar granule cells prevents the onset of apoptosis induced by low potassium. *Neurosci.Lett*. 2000, 283:41–44.

McConkey DJ, Lin Y, Nutt LK, Ozel HZ, Newman RA: Cardiac glycosides stimulate Ca$^{2+}$ increases and apoptosis in adrogen–independent, metastastic human prostate adenocarcinoma cells. *Cancer Res*. 2000, 60:3807–3812.

Verheye–Dua FA, Bohm L:Influence of apoptosis on the enhancement of radiotoxicity by ouabain. *Strahlenther. Onkol.* 2000. 17:186–191.

Ludens JH, Clark MA, DuCharme DW, Harris DW, Lutzke BS, Mandel F, Mathews WR, Sutter DM, Hamlyn JM: Purification of an endogenous digitalis–like factor from human plasma for structural analysis. *Hypertension* 1991, 17:923–929.

Tymiak AA, Norman JA, Bolgar M, DiDonato GC, Lee H, Parker WL: Physicochemical characterization of a ouabain isomer isolated from bovine hypothalamus. *Proc.Natl.Acad.Sci.USA* 1993, 90:8189–8193.

Bagrov, AY, Fedorova OV, Austin JL, Dmitrieva RI, Anderson DE: Endogenous marinobufagenin–like Immunoreactive factor and Na,K–ATPase Inhibition during voluntary hypoventilation. *Hypertension* 1995, 26:781–788.

Sich B, Kirch U, Tepel M, Zidek W, Schooner W: Pulse pressure correlates in humans with a proscillaridin A immunoreactive compound. *Hypertension* 1996, 27:1073–1077.

Hilton PJ, White RW, Lord GA, Garner GV, Gordon DB, Hilton MJ, Forni LG, McKinnon W, Ismail FM, Keenan M, Jones K, Morden WE: An Inhibitor of the sodium pump obtained from human placentas. *Lancet* 1996, 348:303–305.

Hamlyn CM, Hamilton BP, Manunta P: Endogenous ouabain, sodium balance and blood pressure: a review and a hypothesis. *J.Hypertens*. 1996, 14:151–167.

de Wardener HE: Sodium transport inhibitors and hypertension. *J.Hypertens*. 1996, 14:S9–S18.

Goto A, Yamada K: An approach to the development of novel antihypertensive drugs: potential role of sodium pump inhibitors. *TiPS* 1998, 19:201–204.

Qudri L, Bianchi G, Cerri A, Ferizzi G, Ferrari P, Gobbini M, Melloni P, Sputore S, Torri M: 17β–(3Furyl)–5β–androstane–3β, 14β,17α–triol (PST 2238). A very potent antihypertensive agent with a novel mechanism of action. *J.Med.Chem*. 1997, 40:1561–1564.

Kumada N, Kim T, Ohyama A, Tujino T, Iwai Y, Itoh T, Sugimura K, Nakatani T, Yamamoto K, Kisimoto K: Ouabain–containing Euro–Collins solution prevents acute tubular necrosis following kidney preservation. *Transplant.Proc*. 1994, 26:935.

Taurin, Sebastien, et al. "c–Fox expression in ouabain–treated vascular smooth muscle cells from rat aorta: evidence for an intracellular–sodium–mediated, calcium–independent mechanism." *Journal of Physilogy* 543(3):835–847 (2002).

* cited by examiner

US 6,699,676 B1

USES OF OUABAIN AND OUABAIN-LIKE MOLECULES IN APOPTOSIS RELATED PATHOLOGIES

BACKGROUND OF THE INVENTION

The maintenance of the transmembrane gradient of monovalent cation (high $[K^+]_i$ and low $(Na^+)_i$) is universal property of all nucleated cells and its dissipation is viewed as a hallmark of necrotic-type cell death (1,2). It was shown that a transient and moderate rise of intracellular $Na^+$ concentration in mitogen-treated cells is involved in rejoining DNA strand breaks preceeding DNA synthesis (3), whereas longterm inversion of the intracellular $Na^+/K^+$ ratio blocks macromolecular synthesis and cell cycle progression in the majority of eukaryotic cells studied so far (4–7), including vascular smooth muscle cells (VSMC) (8,9). Much less is known about the role of the trans-membrane gradient of monovalent ions in the triggering and progression of programmed cell death (apoptosis).

Cell shrinkage is one of the initial morphological markers of apoptosis in all types of cells, particularly in VSMC (10). In immune system cells, apoptotic shrinkage is so impressive that the term "shrinkage-mediated necrosis" was originally proposed to describe this type of cell death (11), and the striking increase in density of shrunken cells was used to separate intact from apoptotic cells (12,13). In lymphocytes, the apoptotic cell volume decrease is caused by the loss of KCl (14) and a major organic osmolyte, taurine (15), due to the CD95 receptor-mediated activation of $Cl^-$ and $K^+$ channels and taurine outward transporter (for recent review, see (16)). However, the involvement of perturbation of intracellular ion composition and ionic strength of cytoplasm in the triggering and development of the apoptotic machinery remains unclear. Recently, it was shown that equimolar substitution of extracellular $Na^+$ by $K^+$ protects Jurkat cells from apoptosis induced by Fas-ligand receptors (14), suggesting that dissipation of $K^+$ gradients plays a role in the triggering of apoptosis in immune system cells. Here, we report that in contrast to Jurkat cells, inversion of the $[Na^+]_i/[K^+]_i$ ratio blocks apoptosis of VSMC at a site upstream of caspase-3 independently on transmembrane gradient of monovalent cations and cell volume.

SUMMARY OF THE INVENTION

The present invention relates to methods, compositions and uses thereof for inhibiting apoptosis in a cell and/or increasing a cell's resistance to apoptosis. Preferred cells includes vascular smooth muscle cell (VSMC) and cell from the central nervous system.

More particularly, the invention provides a method for inhibiting apoptosis in a cell, comprising the step of increasing the cell's intracellular $[Na^+]/[K^+]$ ratio.

The invention also provides a method for increasing a cell's resistance to apoptosis comprising the step of increasing the cell's intracellular $[Na^+]/[K^+]$ ratio.

The invention further provides methods for inhibiting caspase-3 biological activity in a cell, blocking induced chromatin cleavage in a cell, and preventing DNA laddering in a cell, each of these methods comprising the step of increasing the cell's intracellular $[Na^+]/[K^+]$ ratio.

The invention also relates to the use of a compound or a composition that is capable of increasing intracellular $[Na^+]/[K^+]$ ratio in a cell, for inhibiting apoptosis in a cell or for increasing the cell's resistance to apoptosis. The compound or the composition may also used for the preparation of a formulation for inhibiting apoptosis in a cell or for increasing a cell's resistance to apoptosis.

The invention further provides a pharmaceutical composition for inhibiting apoptosis in a cell or for increasing a cell's resistance to apoptosis, the composition comprising a compound that is capable of increasing a cell intracellular $[Na^+]/[K^+]$ ratio and a pharmaceutically acceptable carrier or excipient.

The methods and compositions according to the present invention may be particularly useful for the prevention or treatment of numerous pathologies such as angina, myocardial infarction, congestive heart failure, dilated cardiopathy, cardiopathy secondary to infarction, neurodegenerative disorder, including dementia and alzheimer.

DETAILED DESCRIPTION OF THE INVENTION

Results

Inhibitors of the $Na^+,K^+$ Pump Block Apoptosis in VSMC

Figure 1:
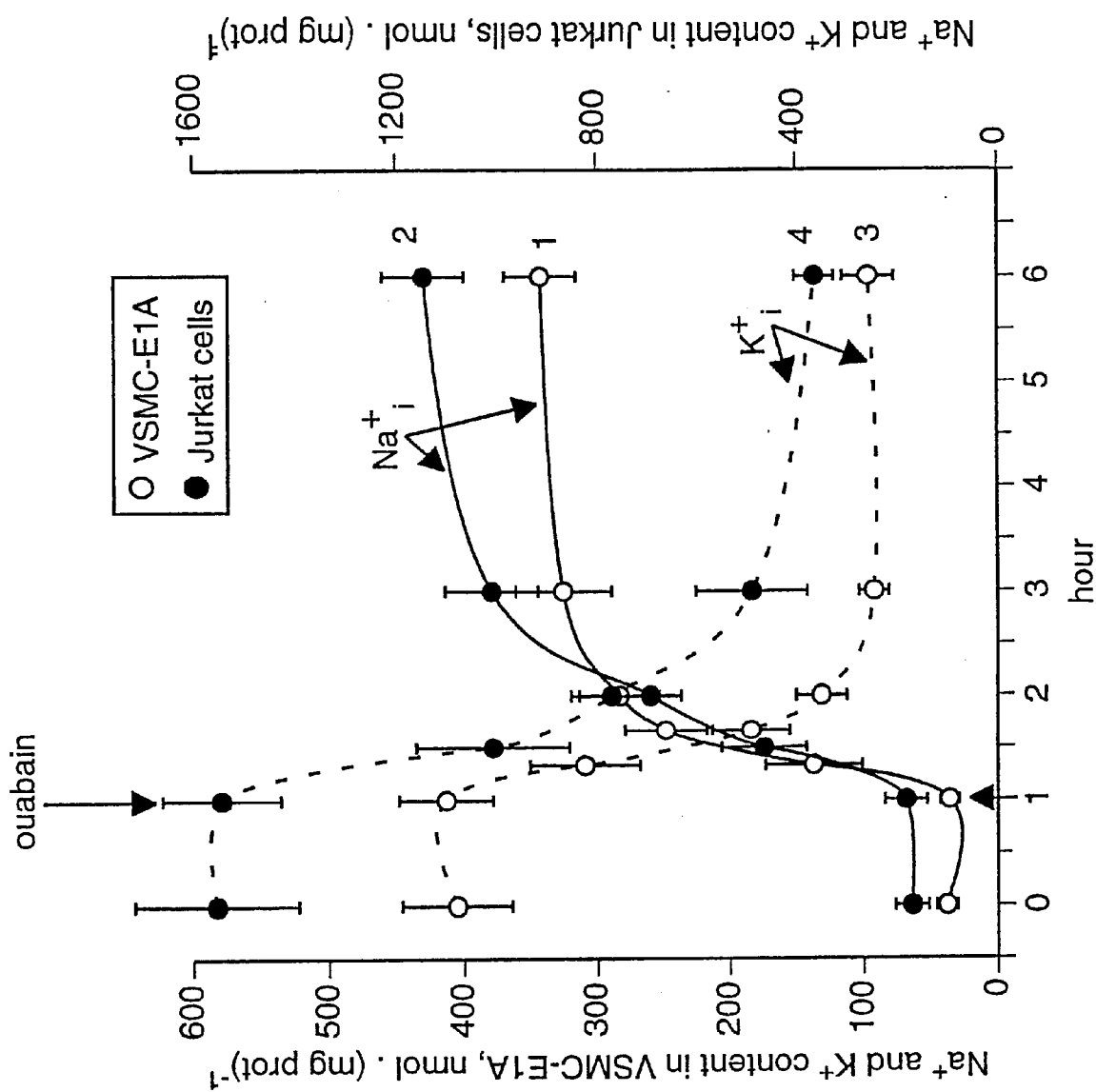
FIG. 1. Kinetics of modulation of intracellular $Na^+$ (1, 2) and $K^+$ (3, 4) content by ouabain in VSMC-E1A (1, 3) and Jurkat cells (2, 4). Cells were preincubated for 24 hours in the presence of 10% calf serum in control medium consisting of 91 mM NaCl, 5 mM KCl, 0.9 mM $NaH_2PO_4$, 44 mM $NaHCO_3$, 1.8 mM $CaCl_2$, 0.8 mM $MgCl_2$, 33 mM HEPES and 5 mM D-glucose (pH 7.4) with 2 $\mu$Ci/ml of $^{22}Na$ or 0.5 $\mu$Ci/ml $^{86}Rb$, and 1 mM ouabain was added at the time interval indicated by the arrow. At specific time-points, intracellular $Na^+$ and K content + was measured as described in Experimental Procedures. Mean values±S.E. obtained in experiments performed in quadruplicate (VSMC-E1A) or triplicate (Jurkat cells) are given.

Previously, it was shown that the activity of apoptotic pathways triggered by serum deprivation can be heightened by transfection of VSMC with c-myc or with its functional analogue E1A-adenoviral protein (VSMC-MYC and VSMC-E1A respectively) (18,19). We used these cells to study the involvement of the $[Na^+]_i/[K^+]_i$ ratio in the regulation of VSMC apoptosis. To increase the $[Na^+]_i/[K^+]_i$ ratio, we inhibited $Na^+,K^+$ pump activity with ouabain or by depletion of incubation medium with $K^+$. In VSMC-E1A, after 2 hours of addition of ouabain intracellular $Na^+$ content was augmented from 38±8 to 283±30 nmol/mg proteins, whereas $K^+_i$ dropped from 405±41 to 131±19 nmol/mg proteins (FIG. 1, curves 1 and 3). Prolongation of incubation with ouabain for up to 5 hours did not significantly modify $Na^+_i$ and $K^+_i$ content in VSMC-E1A. The same kinetics of modulation of $Na^+_i$ and $K^+_i$ content were observed in ouabain-treated Jurkat cells (FIG. 1, curves 2 and 4) and in VSMC incubated in $K^+$-depleted medium (data not shown). A 10-fold increase of the content of intracellular $Na^+$ in ouabain treated Jurkat lymphocytes (FIG. 1, curve 2) is consistent with the same level of elevation of free $Na^+_i$ concentration in human peripheral lymphocytes after inhibition of $Na^+,K^+$ pump in $K^+$-depleted medium and measured with a fluorescent $Na^+$-indicator, SBFI (23). Considering these results, the effect of the $[Na^+]_i/[K^+]_i$ ratio on apoptosis was studied after 1–2 hours of $Na^+,K^+$ pump inhibition.

Figure 2B:
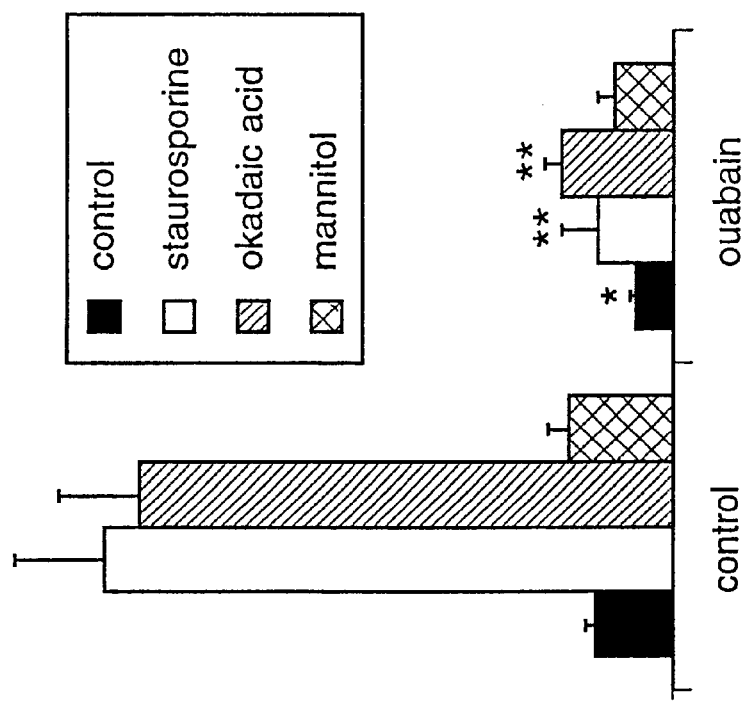
FIG. 2. Effect of ouabain on chromatin cleavage in VSMC-E1A. (A) Kinetics of the accumulation of chromatin fragments in control (curves 1, 3) and ouabain-treated (curves 2, 4) VSMC-E1A in the presence of 10% calf serum (CS, curves 1, 2) or in CS-free medium (curves 3, 4). Mean values ±S.E. obtained in experiments performed in quadruplicate are given. (B) Content of chromatin fragments in VSMC-E1A subjected to 6 hr of incubation in serum-supplied medium with or without 1 mM ouabain, 0.25 $\mu$M staurosporine, 1 $\mu$M okadaic acid and 350 mM mannitol. Mean values±S.E. obtained in 3 experiments performed in quadruplicate are given. ★, ★★ $p<0.05$ and 0.001 compared to ouabain-untreated cells. In both experiments, ouabain was added 1 hour before triggering of apoptosis.
Figure 2A:
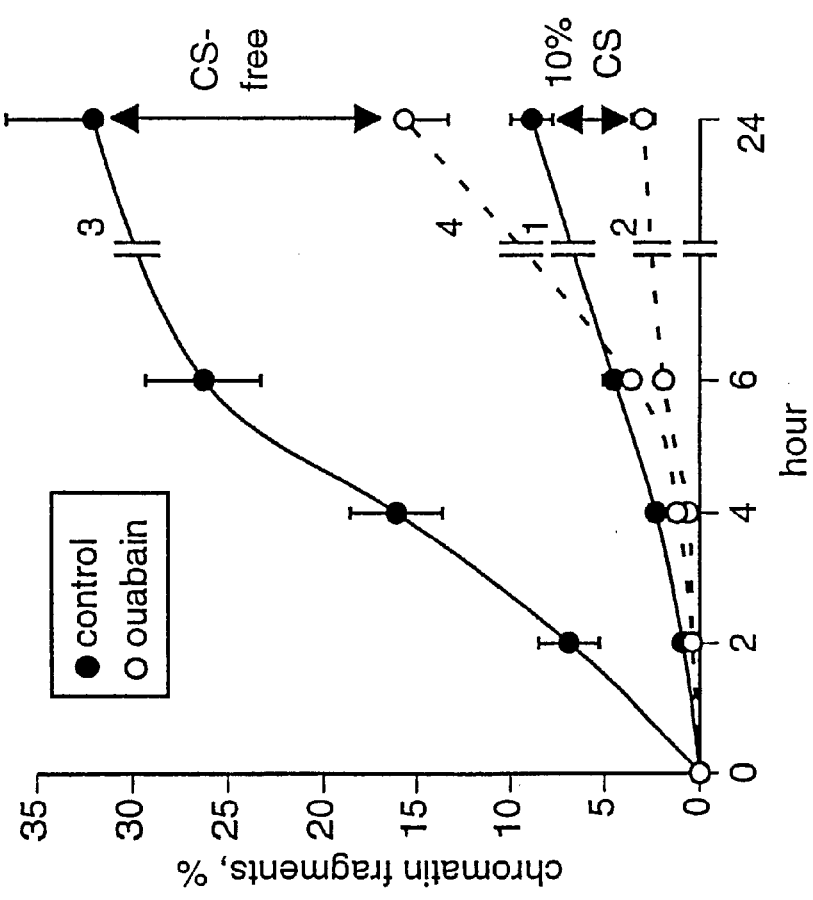

As can be seen from FIG. 2a, serum deprivation drastically potentiated chromatin cleavage in VSMC-E1A, and after 6 hours the content of chromatin fragments was 4.5±0.4 and 26.3±3.0% in control and serum-deprived media, respectively. Treatment with ouabain blocked baseline as well as serum withdrawal-induced chromatin cleavage. Similarly to VSMC-E1A, the antiapoptotic effect of ouabain was also seen in serum-deprived VSMC-MYC as well as in non-transfected VSMC (Table 1). In these experiments, $Na^+,K^+$ pump activity was also blocked by incubation of cells in $K^+$-depleted medium. Like ouabain, this procedure sharply inhibited VSMC apoptosis (Table 1).

FIG. 2b shows that apart from serum withdrawal, VSMC apoptosis can be triggered by inhibitors of protein kinase C (PKC) and serine-threonine phosphatase and after 6 hr of incubation of VSMC-E1A with staurosporine and okadaic acid, the content of chromatin fragments was increased up to 30.1±4.7 and 28.3±4.2%, respectively. Similarly to serum-deprived cells (FIG. 2a), apoptosis. triggered by these compounds was blocked by treatment with ouabain (FIG. 2b). Chromatin cleavage in control and ouabain-treated VSMC-E1A was insensitive to hyperosmotic shrinkage caused by addition of 350 mM mannitol (FIG. 2b). This is consistent with previous results obtained in non-transfected VSMC (10).

Figure 3A:
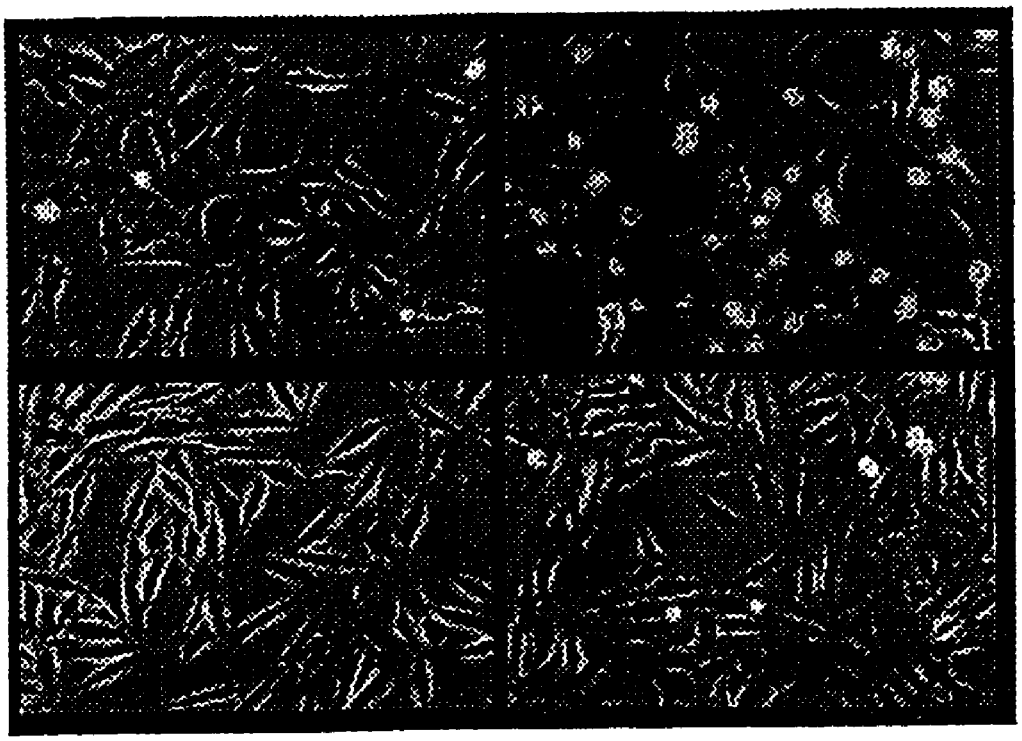
FIG. 3. Effect of ouabain on morphology (A) and DNA laddering (B and C) in VSMC-E1A. In experiments with ouabain, cells were pretreated with 1 mM of this compound 1 hour before 6 hours exposure to serum-free medium. A. Cell morphology was evaluated by phase contrast microscopy without preliminary fixation. a, c) DMEM containing 10% calf serum; b, d) serum-free DMEM; a, b) without ouabain; c, d) in the presence of ouabain. Micro graphs were prepared using a Nikon phase contrast microscope at ×100 magnification. Apoptotic cells are shown by arrows. B. DNA laddering (left part of the figure) was analyzed with a PhosphorImager, and relative content of low molecular weight DNA fragments (1,500–125 bp–right part of the figure) in cells incubated with 10% calf serum (CS) in the absence of ouabain was taken as 100%. Means±S.E. obtained in 2 experiments performed in triplicate are shown.
Figure 3C:
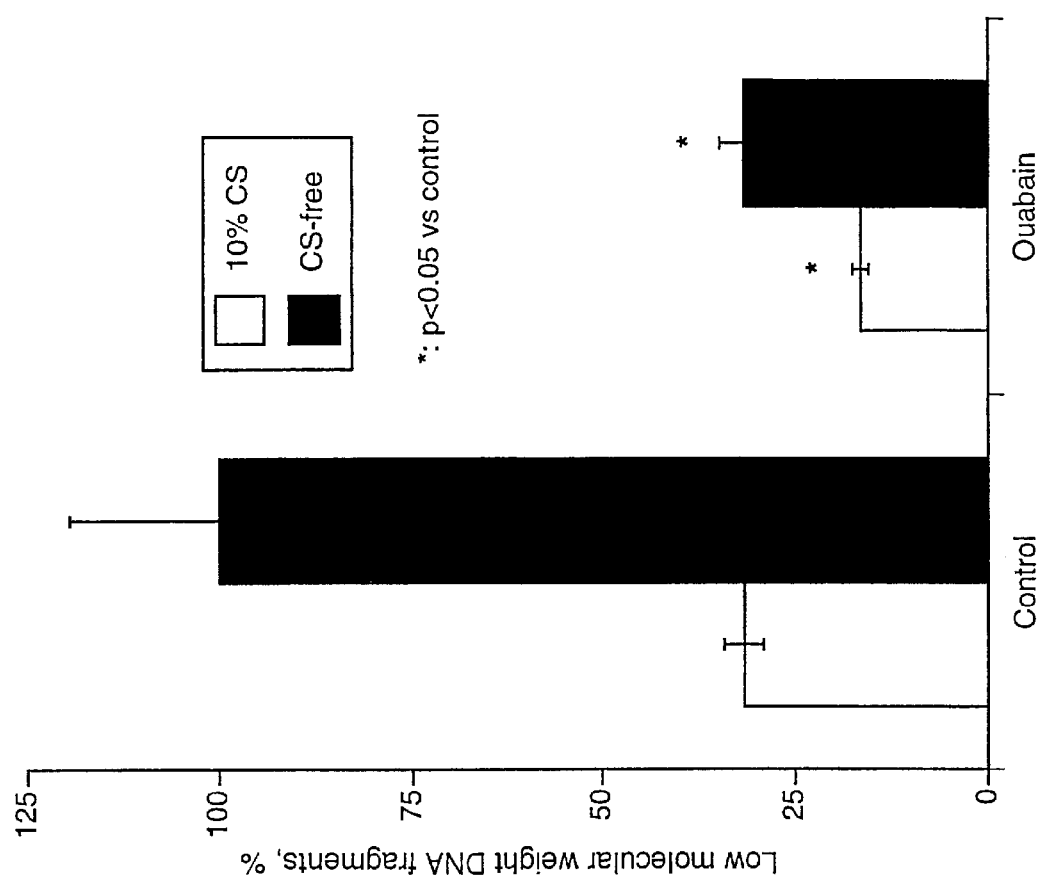
Figure 3B:
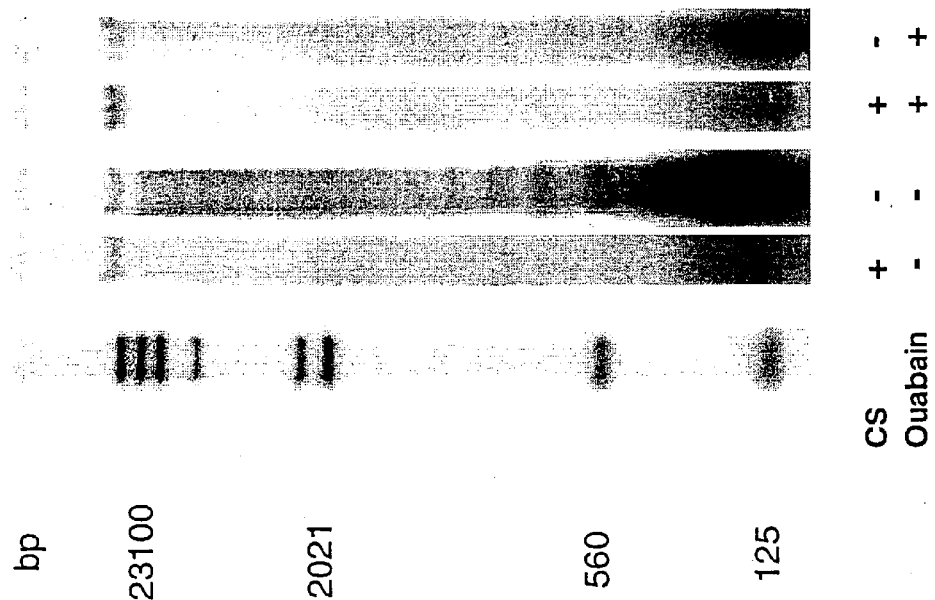

The antiapoptotic action of ouabain in VSMC was further confirmed by phase-contrast microscopy and by analysis of DNA laddering. FIG. 3A shows that pretreatment with ouabain sharply decreased the number of apoptotic cells after 6 hours of incubation of VSMC-E1A in serum-deprived medium. Treatment of VSMC-E1A with ouabain prevented DNA laddering and reduced the accumulation of low molecular weight 3'-end labeled DNA oligonucleosomal fragments triggered by serum deprivation (FIG. 3B). Similar results were obtained with cells that underwent apoptosis in the presence of staurosporine and okadaic acid (data not shown).

Recently, we reported that heat stress triggered necrosis but did not affect apoptosis in VSMC (24). Indeed, as can be seen from Table 2, in contrast to serum-deprived cells, heat stress (46° C., 30 min) did not modulate chromatin cleavage in VSMC but led to a 5-fold increase of lactate dehydrogenase (LDH) release, a marker of necrosis. In contrast to apoptosis, we did not observe modulation by ouabain of heat stress-induced LDH-release. Viewed collectively, these data demonstrate that inhibition of the $Na^+,K^+$ pump protects VSMC against apoptosis but does not affect the necrotic type of cell death.

Ouabain Does Not Affect the Induction of Apoptosis in Jurkat Cells

Figure 4B:
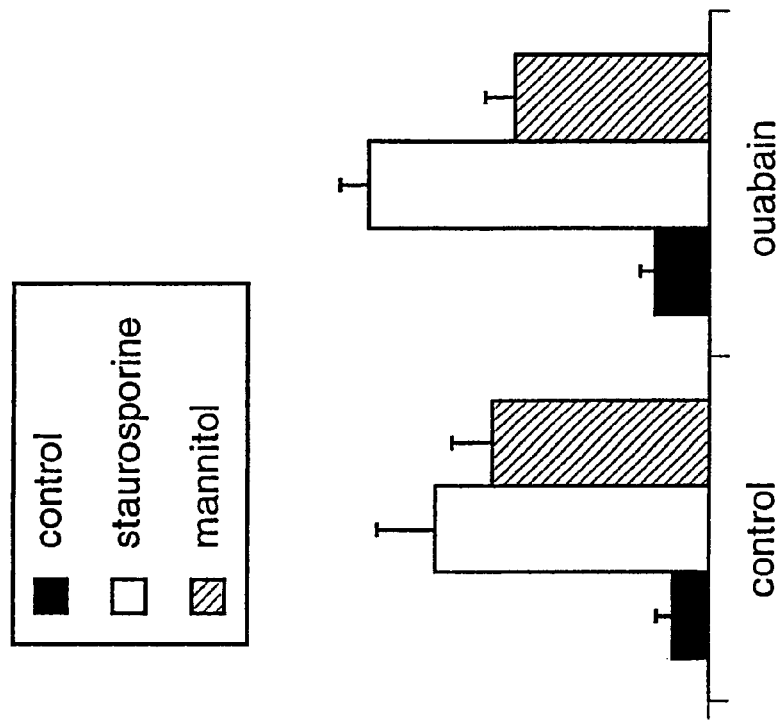
FIG. 4. Effect of ouabain on chromatin cleavage in Jurkat cells. (A) Kinetics of accumulation of chromatin fragments in control (curves 1, 3) and ouabain-treated (curves 2, 4) cells in the absence (curves 1, 2) or presence (curves 3, 4) of 100 ng/ml of anti-human Fas (mouse monoclonal IgM, Upstate Biotechnology, Lake Placid, N.Y.); (B) Content of chromatin fragments in Jurkat cells subjected to 3 hours of incubation with or without 1 mM ouabain, 0.25 µM staurosporine and 350 mM mannitol. In both experiments, ouabain was added 2 hours before triggering of apoptosis. Mean values±S.E. obtained in experiments performed in triplicate are given.
Figure 4A:
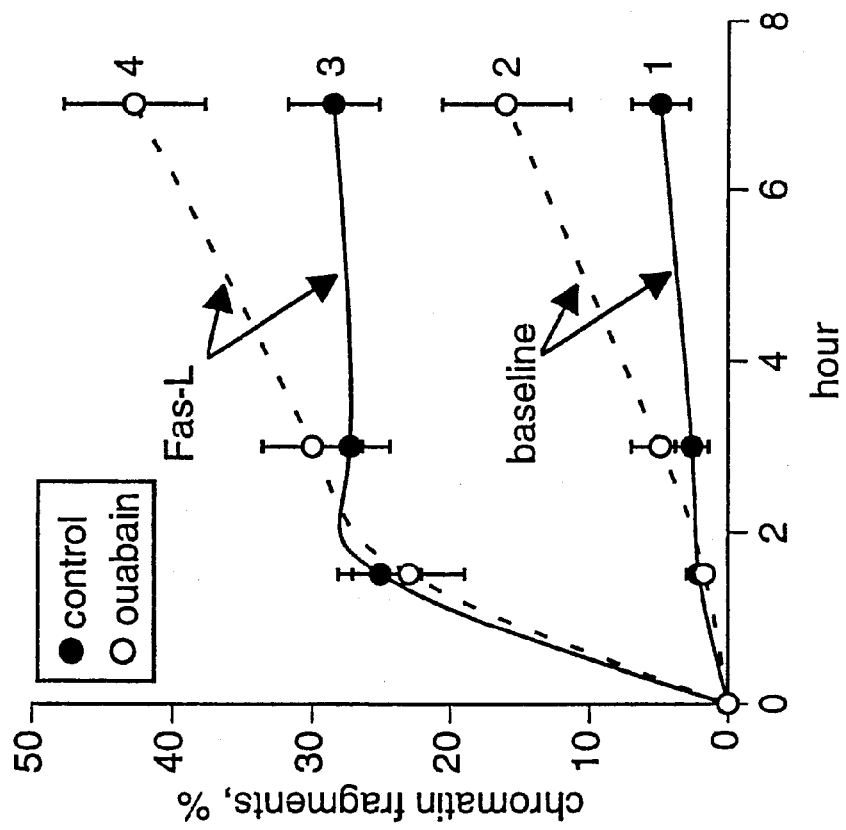

FIG. 4a shows that during 7 hours incubation of Jurkat cells in control medium the content of chromatin fragments was increased monotonously up to ~5%. After 1.5 hour incubation in the presence of Fas ligand (anti-human Fas, mouse monoclonal IgM), the content of chromatin fragments was increased by 10-fold and did not change much during the next 5,5 hours of incubation (FIG. 4a, curve 3). This kinetics is consistent with previously reported data (20,25). Apart from Fas receptor-induced apoptosis playing a key role in the functioning of activated T-lymphocytes, the apoptotic machinery in immune system cells can be triggered by other stimuli, including inhibitors of PKC (14,26) and hyperosmotic shrinkage (27). After 3 hours incubation of Jurkat cells in the presence of 0.25 µM staurosporine or in hyperosmotic medium (addition of 350 mM mannitol), the content of chromatin fragments was increased from 2.6±1.2 to 19.7±4.3 and 15.6±2.9%, respectively (FIG. 4B).

In the absence of triggers of apoptosis, 2 hours pretreatment of Jurkat cells with ouabain did not significantly modify chromatin cleavage after subsequent 3 hours of incubation. Prolongation of incubation with ouabain for up to 7 hours increased the content of chromatin fragments from 4.9±2.1 to 16.0±4.6% (FIG. 4a, curve 2 vs 1). We did not observe any effect of ouabain on the increment of chromatin cleavage triggered by 3 hours treatment of Jurkat cells with Fas ligand, staurosporine or mannitol (FIG. 4b). After 7-hr incubation in the presence of Fas ligand, chromatin cleavage was significantly higher in ouabain-treated cells (FIG. 4a, curves 4 vs 3); however, increment of the content of chromatin fragments triggered by Fas ligand in control and ouabain-treated Jurkat cells was not different (23.6±3.9 and 26.2±4.7%, respectively).

Effect of Equimolar Substitution of Extracellular $Na^+$ by $K^+$

To examine whether or not protection of VSMC cells against apoptosis by inhibition of $Na^+,K^+$-ATPase is mediated by alteration of intracellular $Na^+/K^+$ ratio, we compared the modulation of apoptosis and the intracellular content of $Na^+$ and $K^+$ by ouabain in control ([$Na^+$]=137 mM; [$K^+$]=5 mM) and $K^+$-enriched, $Na^+$-depleted medium ([$Na^+$]=14 MM; [$K^+$]=128 mM). Table 3 shows that in contrast to control medium, neither intracellular content of $Na^+$ and $K^+$ in VSMC-E1A nor baseline apoptosis or apoptosis triggered by serum withdrawal was affected by ouabain in $K^+$-enriched, $Na^+$-depleted medium. Similarly to VSMC-E1A, ouabain did not significantly affect the $[Na^+]_i/[K^+]_i$ ratio in Jurkat cells incubated in $K^+$-enriched, $Na^+$-depleted medium (Table 4). In Jurkat cells, substitution of $Na^+$ by $K^+$ in incubation medium attenuated apoptosis induced by 7-hr treatment with Fas ligand (20.0±2.2 vs 28.5±3.3% in $K^+$-enriched and control medium, respectively), and completely blocked the effect of longterm ouabain administration on baseline chromatin cleavage (5.7±2.0 vs 16.0±4.6% in $K^+$-enriched and control medium, respectively, Table 4).

Modulation of Caspase Activity

Activation of the caspase superfamily protease cascade is involved in apoptotic DNA degradation in the majority of cells studied so far (28,29). However, to the best of our knowledge, there are no data on the measurement of caspase activity in VSMC undergoing apoptosis. Using YVAD-AMC and DEVD-AMC as substrates for the caspase-1 and caspase-3 subfamily (30), we observed that baseline activities of YVAD-ase and DEVD-ase in VSMC-E1A were 1571±256 and 673±235 pmol (mg prot)$^{-1}$ hr$^{-1}$. In these cells, activity of the caspase-1 and caspase-3 measured as YVAD-CHO and DEVD-CHO-sensitive components of YVAD-ase and DEVD-ase, respectively, was 56±47 and 547±111 pmol (mg prot)$^{-1}$ hr$^{-1}$ (n=9). In Jurkat cells total YVAD-ase and DEVD-ase activity was 1,830±201 and 831±95 pmol (mg prot)$^{-1}$ hr$^{-1}$, whereas caspase-1 and caspase-3 activity was in the range of 121±67 and 305±41 pmol (mg prot)$^{-1}$ hr$^{-1}$, respectively (n=12) that is in accordance with previously reported data (31).

Figure 5A:
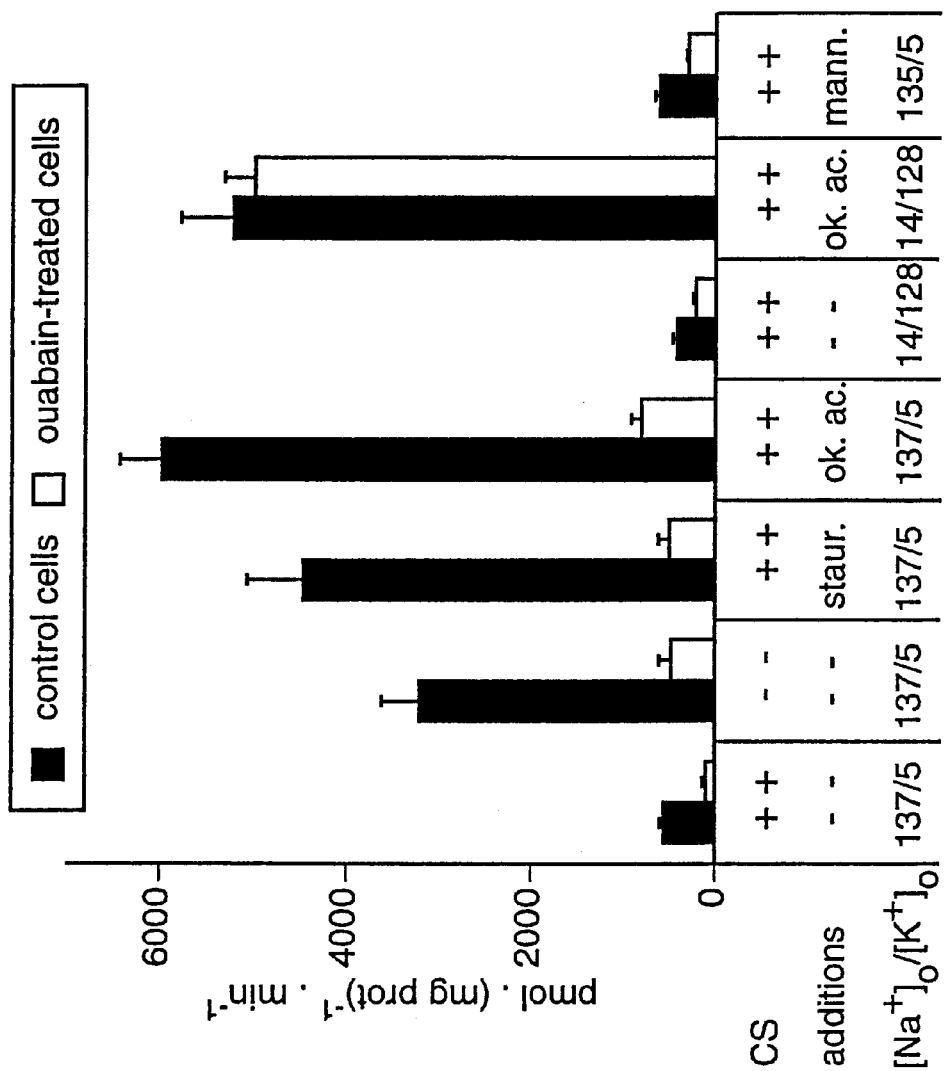
FIG. 5. Effect of ouabain on caspase-3 activity in VSMC-E1A (A) and Jurkat cells (B). VSMC-E1A and Jurkat cells were pretreated with 1 mM ouabain for 1 and 2 hours, respectively, and the additions indicated below the bars were delivered in media with 10% calf serum and with the baseline (137/5) or inverse (14/128) $[Na^+]_o/[K^+]_o$ ratio for 6 (VSMC-E1A) or 3 hours (Jurkat cells). In experiments with VSMC-E1A, calf serum (CS) was omitted where indicated (−). Abbreviations: staur.—staurosporine (0.25 µM), ok.ac.—okadaic acid (1 µM), mann.—mannitol (350 mM); Fas-L—Fas ligand (100 ng/ml). Mean values±S.E. obtained in experiments performed in quadruplicate (A) or triplicate (B) are given. ★p<0.001 compared to ouabain-untreated cells.

Neither Jurkat cells nor VSMC-E1A undergoing apoptosis showed modulation of caspase-1 activity (data not presented). In contrast to caspase-1, caspase-3 activity in VSMC-E1A was increased after 6 hours incubation in serum-deprived medium or in the presence of staurosporine and okadaic acid by 6-, 8- and 10-fold, respectively, but was insensitive to mannitol-induced cell shrinkage (FIG. 5A). Pretreatment of VSMC-E1A for 1 hour with ouabain decreased the baseline activity of caspase-3 from 560±41 to 101±39 pmol (mg prot)$^{-1}$ hr$^{-1}$ ($p<0.001$) and abolished the increment of caspase-3 activity under induction of apoptosis (FIG. 5A). We did not observe any effect of ouabain on caspase-3 activity in VSMC-E1A undergoing apoptosis triggered by okadaic acid in $K^+$-enriched, $Na^+$-depleted medium ($[Na^+]_o/[K^+]_o=14/128$) (FIG. 5A). Similar negative results were obtained with serum-deprived VSMC-E1A and VSMC-E1A treated with staurosporine in $K^+$-enriched, $Na^+$-depleted medium (data not shown).

Figure 5B:
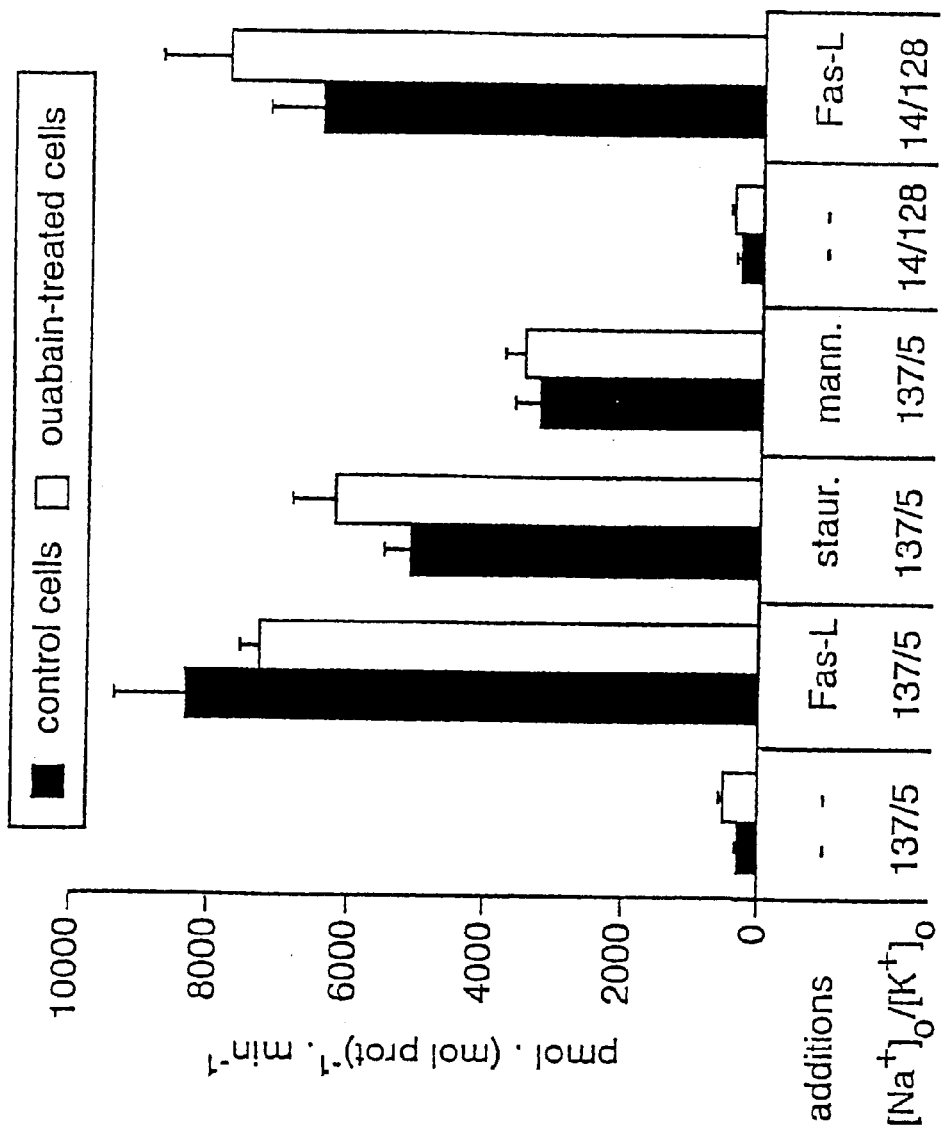

In Jurkat cells, caspase-3 activity was increased by ~30-, 20- and 10-fold after 3 hours of treatment with Fas ligand, staurosporine and mannitol, respectively. Pretreatment of Jurkat cells for 2 hours with ouabain increased baseline caspase-3 activity from 296±38 to 497±67 pmol (mg prot)$^{-1}$ hr$^{-1}$. Neither ouabain nor equimolar substitution of $Na^+$ by $K^+$ in the incubation medium affected the increment of caspase-3 activity in Jurkat cells triggered by Fas ligand, staurosporine and hyperosmotic shrinkage (FIG. 5B).

Oubain-like Molecules Activities

Referring to FIG. 5, to further confirm that ouabain (1β,3β,5,11α,14,19-hexahydroxycard 20 [22]-enolide 3-[6-deoxy-α-L-mannopyrano-sidel]) blocks VSMC apoptosis via inhibition of $Na^+,K^+$ pump and inversion of $Na^+_i/K^+_i$ ratio rather than by its direct effect on apoptotic pathways, we compared chromatin cleavage in VSMC treated with ouabain and other inhibitor of $Na^+,K^+$ pump, such as digitoxin(5β,20[22]-cardenolide-3β,14-diol-3[O-2,6-dideoxy-β-D-ribohexopyranosyl-(1->4)-2, 3-dideoxy-β-D-ribohexo-pyranosyl]oxy) and digoxin (12β-hydroxy-digitoxin).

Data presented in Table 5 show that all these compounds inhibited serum-deprivation-induced chromatin cleavage to the same extend, thus indicating a key role of the inhibition of $Na^+,K^+$ pump and inversion of $Na^+_i/K^+_i$ ratio in protection of VSMC from apoptosis.

Potential of the Application of the Molecules Able to Prevent Apoptosis

Current digitalis and ouabain-like molecules have the capacity to improve myocardial function but do not impact on the final outcome of cell survival; due to their arythmogenic potential, which may negate any benefit of myocardial protection.

The following oubain-like molecules are encompassed by the present invention:
Digoxin (Digoxigenin)
Digitoxin (Digitoxigenin)
Acetyldigoxin
Acetyldigitoxin
Gitaloxin (Gitoxigenin)
Deslanosid
Lanatosid C
Ouabagenin
Scillaren
Strophantin
Proscillaridin
Thevetosid
Bufanin
Bufadienolid Derivatives of digitalis/ouabain can be constructed to reduce their arythmogenic effect and further enhance anti-apoptotic capacity with as outcome.

The present invention concerns a method for protection of apoptosis related pathologies selected from the group of myocardial cells in acute ischemic episodes, chronic situations, central nervous system cells in diseases dementia, alzheimer, neurodegenerative disorder or trauma, reperfusion injury of solid parenchymatosed organs, acute trauma, or acute or chronic renal failure, comprising administering a pharmaceutical effective amount of oubain or an oubain-like molecule.

The oubain and oubain-like molecules are useful for protection of (1) myocardial cells in acute (ischemic) episodes such as accelerated angina, myocardial infection; (2) chronic situations, including congestive heart failure, dilated cardiopathy, cardiopathy secondary to infarction; (3) central nervous system cells in diseases dementia, alzheimer, neurodegenerative disorder and trauma; (4) reperfusion injury of solid parenchymatosed organs; (5) acute trauma including severe burn protection and other situatoins of increased apoptosis; and (6) acute and chronic renal failure.

According to the present invention, the oubain and oubain-like molecules are used in the above mentioned pharmaceutical applications in non-toxic and pharmaceutical acceptable concentration determined by clinical assays. These molecules has already been tested and such concentrations are known in the field of the invention.

Results Analysis

The data obtained and presented herein above show for the first time that independently of the origin of apoptotic signals and transfection with c-myc or its functional analogue E1A-adenoviral protein, inhibition of the $Na^+,K^+$ pump blocks the development of apoptosis in VSMC (FIGS. 2 and 3) without any modulation of VSMC necrosis triggered by severe heat stress (Table 2). In contrast to VSMC, 2 hours preincubation with ouabain in the absence of triggers of apoptosis following 3 hours incubation in the presence of three different apoptotic stimuli (Fas ligand, staurosporine and cell shrinkage with mannitol) did not modulate apoptosis in Jurkat cells (FIG. 4). Prolongation of incubation with ouabain for up to 7 hours resulted in the activation of baseline chromatin cleavage in Jurkat cells but did not affect the increment of accumulation of chromatin fragments triggered by activation of the Fas receptor (FIG. 4a). Our results on the activation of baseline apoptosis under 7 hours inhibition of the $Na^+,K^+$ pump in Jurkat cells are consistent with recent data on the induction of apoptotic DNA degradation in human peripheral lymphocytes treated with ouabain for 48 hours (32). The potentiation of baseline apoptosis after longterm treatment of immune system cells with ouabain may be caused by the rise of intracellular $Ca^{2+}$ concentration due to activation of the $Na^+_i/Ca^{2+}_o$ mode of operation of $Na^+/Ca^{2+}$ exchanger which is highly active in human T-lymphocytes (33) and in Jurkat cells (34). This hypothesis is supported by prevention of the induction of baseline apoptosis in Jurkat cells treated with ouabain in $Na^+$-depleted medium (Table 4), i.e. under inhibition of the $Na^+_i/Ca^{2+}_o$ mode of operation of $Na^+/Ca^{2+}$ exchanger, and is consistent with numerous data on the implication of sustained elevation of $[Ca^{2+}]_i$ in triggering of apoptosis in immune system cells (35,36). In contrast to immune system cells, we did not observe any effect of moderate elevation of $[Ca^{2+}]_i$ by thapsigargin and ionomycin on VSMC apoptosis (37).

Our results show that inhibition of apoptosis by ouabain in VSMC is caused by inversion of the $[Na^+]_i/[K^+]_i$ ratio rather than by $Na^+_i/K^+_i$-independent modulation of ion current and membrane potential mediated by electrogenic $Na^+, K^+$ pump. Indeed, suppression of VSMC apoptosis by ouabain was abolished in $K^+$-enriched $Na^+$-depleted medium, i.e. when inhibition of the $Na^+,K^+$ pump did not affect intracellular $Na^+$ and $K^+$ content (Table 3). As with ouabain, VSMC apoptosis was blocked by inhibition of the $Na^+,K^+$ pump in $K^+$-depleted medium (Table 1). We did not observe any significant effect of 8 hours incubation of VSMC with ouabain on LDH release (Table 2), ATP content and protein synthesis (data not shown). DNA synthesis in VSMC, measured as serum-induced [$^3$H]-thymidine incorporation, was also insensitive to 5 hours preincubation with ouabain and was decreased by ~60% only after 48 hours of the $Na^+, K^+$ pump inhibition (data not presented). Viewed collectively, these results rule out the possible side-effects of ouabain on VSMC as well as the toxic effect of 1 inversion of the $[Na^+]_i/(K^+]_i$ ratio.

It may be assumed that inversion of the $[Na^+]_i/[K^+]_i$ ratio blocks VSMC apoptosis via inhibition of net $K^+$ efflux involved in cell shrinkage revealed in most of cells undergoing programmed cell death, including VSMC (10). This hypothesis is based on the induction of apoptotic DNA degradation in hyperosmotically-shrunken mouse lymphoma cells, rat thymocytes (27) and Jurkat cells (14). Similar results were obtained study by analysis of the effect of mannitol-induced shrinkage on chromatin cleavage in Jurkat cells (FIG. 4b). Moreover, like other inducers of apoptosis, hyperosmotic shrinkage led to activation of caspase-3 in Jurkat cells (FIG. 5B). However, neither chromatin cleavage (FIG. 3b) nor caspase-3 activity (FIG. 5A) was affected by mannitol-induced shrinkage of VSMC-E1A. These results underlie a cell-specific impact of shrinkage in apoptosis and demonstrate a cell volume-independent mechanism of inhibition of VSMC apoptosis by inversion of the $[Na^+]_i/[K^+]_i$ ratio. Under analysis of this data it should be mentioned that hyperosmotic shrinkage leads to rapid clustering and ligand-independent activation of receptor tyrosine kinases, including TNF-receptors (38). Based on these results, the induction of apoptosis in immune system cells in hyperosmotic medium may be viewed as a consequence of clustering and activation of Fas receptors (16). Considering this, it may be suggested that lack of the effect of hyperosmotic medium on VSMC apoptosis is caused by the absence of functionally active death domain receptors. Indeed, neither Fas nor TNF-α were able to trigger apoptosis in VSMC from normal vessels (39,40) as well as in E1A-transfected VSMC.

Dissipation of the transmembrane gradient of monovalent cations caused by $Na^+,K^+$ pump inhibition can affect apoptosis via membrane depolarization and conformational transition of membrane-bound proteins involved in triggering of apoptotic machinery. In this case, it can be predicted that similarly to ouabain-treated VSMC, apoptosis can also be blocked by a rise of extracellular $K^+$ concentration. Indeed, suppression of apoptosis by equimolar substitution of $Na^+_o$ with $K^+_o$ was observed in Jurkat cells treated with 10 ng/ml anti-human Fas IgM (14). The above reported results show that equimolar substitution of $Na^+_o$ by $K^+_o$ led to 30–40% inhibition of the increment of chromatin cleavage triggered by treatment of Jurkat cells with 100 ng/ml anti-human Fas IgM (Table 4). However, in contrast to Jurkat cells, equimolar substitution of $Na^+_o$ by $K^+_o$ did not protect ouabain-untreated VSMC-E1A from apoptosis triggered by serum withdrawal (Table 3). These results strongly suggest that inversion of the $[Na^+]_i/[K^+]_i$ ratio blocks VSMC apoptosis independently of modulation of the $Na^+$ and $K^+$ electrochemical gradient across the plasma membrane.

It has been reported that suppression of apoptosis in ouabain-treated VSMC-E1A is accompanied by inhibition of caspase-3 activity (FIG. 5A). Thus, it may be assumed that the increased $[Na^+]_i/[K^+]_i$ ratio blocks VSMC apoptosis via direct inhibition of the activity of this enzyme. To examine this hypothesis, we measured the activity of caspases in lysates of VSMC-E1A subjected to 6 hours serum withdrawal has been measured. Both caspase-3 and caspase-1 activity was decreased by 10–20% by the addition of 100 mM KCl; however, the same level of inhibition was also observed under addition of 100 mM NaCl or choline chloride (data not shown). Thus, it may be concluded that the rise in ionic strength slightly inhibits caspases, whereas the $Na^+/K^+$ ratio did not affect enzyme activity.

It is well-documented that activation of caspase-3 by Fas ligand is caused by cleavage of procaspase-3 triggered by FADD-mediated activation of caspase-8 (41) and is independent of cytochrome C release from mitochondria (42). However, as it was mentioned above Fas ligand signaling pathway is quenched in VSMC and VSMC-E1A. In several cell types, Fas-independent cleavage of procaspase-3 is triggered by caspase-9 which in turn is activated by Apaf-1-cytochrome C complex (41). At least in HeLa cells, cytochrome C release is caused by caspase-8-mediated proteolysis of Bid, a BH3 domain-containing protein which interacts with both Bax and bcl-2 (43) and is independent of dissipation of mitochondrial transmembrane potential (44). Recently, it was proposed that procaspase-3 activity is controlled by the $Na^+/K^+$ ratio (31). This hypothesis was based on the selective inhibition by KCl of caspase-3 activity in rat thymocyte lysates treated with 10 μg/ml cytochrome C and 1 mM dATP. However, the effect of these compounds at the same concentration on caspase-3 activity in VSMC-E1A lysates in the absence of monovalent cations as well as in the presence of 100 mM KCl or NaCl has not been detected (data not shown). Viewed collectively, these results demonstrate that the $[Na^+]_i/[K^+]_i$ ratio blocks VSMC apoptosis at a site upstream of caspase-3.

In conclusion, the above mentioned results show that inversion of the $[Na^+]_i/[K^+]_i$ ratio blocks apoptosis in VSMC via inhibition of trigger-independent steps of the programmed death machinery at a site upstream of the caspase-3-triggering cascade. Comparison of the requirement for caspase-9 and caspase-3 in fibroblasts and immune systems cells treated with UV and γ-irradiation, staurosporine or anti-CD95 indicates the existence of at least four different types of apoptosis (45). Data obtained and detailed herein above show that caspase-3-dependent apoptosis may be further subclassified based on its sensitivity to the $[Na^+]_i/[K^+]_i$ ratio and cell volume. In VSMC, caspase-3-dependent apoptosis can be blocked by increment of the $[Na^+]_i/[K^+]_i$ ratio but is insensitive to cell shrinkage. In contrast, in Jurkat cells, cell shrinkage activates caspase-3-dependent apoptosis whereas the $[Na^+]_i/[K^+]_i$ ratio does not affect apoptosis triggered by Fas ligand, staurosporine or cell shrinkage.

TABLE 1

Effect of ouabain and $K^+$-depleted medium on chromatin cleavage in non-transfected VSMC and in VSMC transfected with c-myc and E1A-adenovirus.

| | Chromatin fragments (%) | | | | | |
|---|---|---|---|---|---|---|
| | VSMC | | VSMC-MYC | | VAMC-E1A | |
| Incubation medium | 10% CS | CS-free | 10% CS | CS-free | 10% CS | CS-free |
| 1. Control | 1.9 ± 0.3 | 6.6 ± 0.9 | 2.7 ± 0.5 | 15.9 ± 1.5 | 4.1 ± 0.4 | 28.3 ± 3.6 |
| 2. Ouabain | 1.6 ± 0.3 | 2.5 ± 0.6** | 1.4 ± 0.3 | 3.1 ± 0.4** | 1.5 ± 0.3* | 5.7 ± 0.6** |
| 3. $K^+$-depletion | 1.7 ± 0.4 | 2.4 ± 0.4** | 1.6 ± 0.4 | 3.5 ± 0.7** | 1.9 ± 0.2* | 5.8 ± 1.9** |

Cells were incubated in $K^+$-containing medium consisting of 91 mM NaCl, 5 mM KCl, 0.9 mM $NaH_2PO_4$, 44 mM $NaHCO_3$, 1.8 mM $CaCl_2$, 0.8 mM $MgCl_2$, 33 mM HEPES and 5 mM D-glucose (pH 7.4) (lines 1 and 2) or in $K^+$-depleted medium (equimolar substitution of KCl by NaCl, line 3) with or without 10% calf serum (CS) and 1 mM ouabain as indicated. In experiments with VSMC-MYC and VSMC-E1A, cells were preincubated for 1 hr with ouabain or with $K^+$-depleted medium in the presence of CS and then subjected to treatment with serum-free media. After 24 hours (VSMC) or 6 hours (VSMC-MYC and VSMC-E1A), the content of chromatin fragments was measured as described in Experimental Procedures. Mean values±S.E. obtained in 3 experiments performed in quadruplicate (VSMC) or triplicate (VSMC-MYC, VSMC-E1A) are given. ★, ★★ p<0.05 and 0.001 compared to the controls.

TABLE 2

Effect of ouabain on chromatin cleavage and LDH release in serum-deprived and heat-treated VSMC.

| | Chromatin fragments (%) | | LDH release (%) | |
|---|---|---|---|---|
| | Control cells | Oaubain-treated cells | Control cells | Ouabain treated cells |
| 1. Serum-supplied | 2.3 ± 0.4 | 1.3 ± 0.4* | 1.1 ± 0.4 | 1.2 ± 0.3 |
| 2. Serum-deprived cells | 4.5 ± 0.7 | 1.8 ± 0.3** | 2.2 ± 0.5 | 1.8 ± 0.4 |
| 3. Serum-supplied, heat-treated cells | 2.3 ± 0.6 | 1.6 ± 0.4 | 10.2 ± 2.4# | 11.0 ± 2.8# |

VSMC growing in 6-well (LDH release) or 24-well (chromatin cleavage assay) plates were preincubated for 3 hours with or without 1 mM ouabain. In part of the experiments, the cells were subjected to 30 min incubation at 46° C. (heat-treated cells, line 3). They were then incubated in the absence (line 2) or presence (lines 1, 3) of 10% calf serum during additional 8 hr and chromatin cleavage and LDH release were measured as indicated in Experimental Procedures and with a spectrophotometric kit (Sigma), respectively. Means±S.E. from experiments performed in triplicate (LDH release) or quadruplicate (chromatin cleavage) are given. ★, ★★ p<0.05 and 0.001 compared to ouabain-untreated cells. #p<0.001 compared to serum-supplied, heat-untreated cells.

$Na^+$-enriched solution containing 0.5 $\mu$Ci/ml $^{86}$Rb or 2 $\mu$Ci/ml $^{22}$Na, and an additional 6 hours incubation in $Na^+$—(line 1) or $K^+$—(line 2) enriched medium containing 10% calf serum, isotopes with the same specific activity with or

TABLE 3

Effect of equimolar substitution of extracellular
$Na^+$ by $K^+$ on intracellular monovalent cation content and
chromatin cleavage in control and ouabain-treated VSMC-E1A

| Concentration of | Intracellular cations (nmol/mg prot) | | | | Chromatin fragments (%) | | | |
|---|---|---|---|---|---|---|---|---|
| $Na^+$ and $K^+$ in incubation | Control cells | | Ouabain-treated cells | | Control cells | | Ouabain-treated cells | |
| medium (mM) | $Na^+_i$ | $K^+_i$ | $Na^+_i$ | $K^+_i$ | 10% CS | CS-free | 10% CS | CS-free |
| 1. $[Na^+]_O = 137$; $[K^+]_O = 5$ | 42 ± 14 | 297 ± 36 | 312 ± 47* | 99 ± 21* | 5.2 ± 0.6 | 32.8 ± 4.8 | 1.9 ± 0.5* | 6.3 ± 1.4 |
| 2. $[Na^+]_O = 14$; $[K^+]_O = 128$ | 38 ± 11 | 311 ± 40 | 51 ± 18 | 293 ± 36 | 5.9 ± 1.0 | 34.6 ± 5.0 | 5.0 ± 0.8 | 32.0 ± 5.5 |

To estimate chromatin cleavage, cells were incubated for 1 hr in the presence of 10% calf serum (CS) in the control solution (DMEM, $[Na^+]$=137 mM; $[K^+]$=5 mM—line 1) or under equimolar substitution of NaCl by KCl ($[Na^+]$=14 mM; $[K^+]$=128 mM—line 2) with or without 1 mM ouabain and then for an additional 6 hours in the same media with or without CS. Intracellular $Na^+$ and $K^+$ content was measured as steady-state distribution of isotopes after 24 hours preincubation of cells in control $Na^+$-enriched solution containing 0.5 $\mu$Ci/ml $^{86}$Rb or 2 $\mu$Cilml $^{22}$Na, and additional 6 hours incubation in $Na^+$—(line 1) or $K^+$—(line 2) enriched medium, containing 10% CS and isotopes with the same specific activity with or without 1 mM ouabain. For more details see Experimental Procedures. Mean values±S.E. obtained in 3 experiments performed in triplicate (ion content) or quadruplicate (chromatin cleavage) are given. ★p<0.001 compared to ouabain-untreated cells.

without 1 mM ouabain. For more details see Experimental Procedures. Mean values±S.E. obtained in experiments performed in triplicate are given. ★, #p<0.01 and 0.001 compared to ouabain-untreated cells.

TABLE 5

Effect of ouabain, digoxin and digitoxin on apoptosis in VSMC-E1A cells.

| Additions (mM) | Increment of chromatin fragments triggered by serum withdrawal(%) |
|---|---|
| None (control) | 100 ± 11 |
| Ouabain, 1 | 21 ± 3* |
| Digoxin, 1 | 18 ± 4* |
| Digitoxin, 1 | 24 ± 6* |

TABLE 4

Effect of equimolar substitution of extracellular
$Na^+$ by $K^+$ on intracellular monovalent cation content and
chromatin cleavage in control and ouabain-treated Jurkat cells.

| Concentration of $Na^+$ and $K^+$ | Intracellular cations (nmol/mg protein) | | | | Chromatin fragments (%) | | | |
|---|---|---|---|---|---|---|---|---|
| in incubation medium | Control cells | | Ouabain-treated cells | | Control cells | | Ouabain-treated cells | |
| (mM) | $Na^+_i$ | $K^+_i$ | $Na^+_i$ | $K^+_i$ | control | +Fas-L | control | +Fas-L |
| 1. $[Na^+]_{O=137}$; $[K^+]_O = 5$ | 183 ± 33 | 1545 ± 96 | 1137 ± 10# | 107 ± 21# | 4.9 ± 2.1 | 28.5 ± 2.1 | 16.0 ± 4.6* | 42.7 ± 5.0* |
| 2. $[Na^+]_{O=14}$ $[K^+]_{O=128}$ | 162 ± 33 | 1584 ± 99 | 204 ± 30 | 498 ± 47 | 4.0 ± 0.6 | 20.2 ± 2.2 | 5.7 ± 2.0* | 22.7 ± 5.3* |

To estimate chromatin cleavage, cells were incubated for 2 hours in the presence of 10% calf serum in the control solution (DMEM, $[Na^+]$=137 mM; $[K^+]$=5 mM—line 1) or under equimolar substitution of NaCl with KCl ($[Na^+]$=14 mM; $[K^+]$=128 mM—line 2) with or without 1 mM ouabain and then for an additional 7 hours at the same media with or without 100 ng/ml Fas ligand (Fas-L). Intracellular $Na^+$ and $K^+$ content was measured as steady-state distribution of isotopes after 24 hours preincubation of cells in control VSMC-E1A cells were pretreated with compounds indicated in the left column during 2 hours in DMEM containing 10% calf serum and then additional 3 hours in the absence or presence of calf serum. The increment of the content of chromatin fragments triggered by serum withdrawal in control cells was taken as 100%. Means+S.E. from experiments performed with quadruplicate are given. ★p<0.001 as compared to control.

EXAMPLES

Cells. VSMC were obtained by explant methods from aortas of 10- to 13-week-old male rats as described previously (17), cultured in DMEM with 10% calf serum, 100 U/ml penicillin, 100 g/ml streptomycin and used between 10 to 16 passages. Cells transfected with c-myc (VSMC-MYC) and E1A-adenovirus (VSMC-E1A) were obtained in accordance with a previously-described protocol (18,19) and were cultured in the same medium with the addition of 500 g/ml genticin. Jurkat cells were obtained from the American Type Culture Collection and cultured in RPMI 1640 medium supplied with 10% calf serum, antibiotics, sodium pyruvate, glutamate and β-mercaptoethanol.

Chromatin cleavage assay. Chromatin cleavage in VSMC was estimated by a technique described previously in detail (10). Briefly, VSMC grown in 24-well dishes were labeled for 24 hours in serum-supplied DMEM with [$^3$H]-thymidine (1 μCi/ml), washed with 2×2 ml of DMEM and incubated in serum-supplied DMEM. In 48 hr, the cells were pretreated with ouabain or K$^+$-depleted medium as indicated in FIG. 2 and Table 3, washed twice with serum-containing medium and incubated with 0.5 ml of medium with or without ouabain and containing different inducers of apoptosis. To measure the content of chromatin fragments, the cells were transferred on ice and 1 ml of ice-cold lysed buffer (10 mM EDTA, 10 mM tris-HCl, 0.5% triton X100 (pH 8.0)) was added. After 15 min, the cell lysate was transferred to Ependorf tubes, sedimented (12,000 rpm, 10 mm), and 1 ml of supernatant was transferred for the measurement of radioactivity ($A_{1t}$). The remaining radioactivity from pellets and wells was extracted with 0.5 ml of 1% SDS/4 mM EDTA mixture, combined and counted (A2). Chromatin cleavage was quantified as the content of chromatin fragments normalized by total content of [$^3$H]-labeled DNA in accordance with the equation $[1.5\times(A_{1t}-A_{1o})/(A_2+A_{1t}-1.5A_{1o})]\times 100\%$ where $A_{1o}$ is the value of $A_{1t}$ before induction of apoptosis. To measure chromatin fragmentation in [$^3$H]-thymidine-labeled Jurkat cells, they were resuspended at a density of 10$^6$ cells/ml in medium containing 10% calf serum and the additions indicated in FIG. 4 and Table 4. At the time intervals shown in FIG. 4, 100 μl of cell suspension was mixed with 100 μl of PBS contairung 0.5% triton X100, and the content of chromatin fragments was measured as described previously in detail (20).

3'-end DNA labeling. VSMC-E1A seeded in 75 cm$^2$ flasks were treated with 4 ml of lysis buffer containing 50 mM tris-HCl, 20 mM EDTA (pH 8.0), 0.5% SDS and 500 μg/ml proteinase K. The lysate was incubated at 50° C. for 3 hours, mixed with 250 μg/ml RNAase A and incubated for 1 hour at 37° C. After phenol-chloroform extraction, DNA was precipitated by the addition of mixture containing 500 mM K-acetate and ethanol (1:2, v:v). The precipitate was resuspended in water and 1 μg of DNA was mixed with a solution containing 2 mM CoCl$_2$, 0.2 mM dithiothreitol, 100 mM K-cacodilate, 0.5 mM [$^{32}$P]dCTP (3000 Ci/mmol) and 15 U/μl terminal deoxynucleo-tidyl transferase (tdt, final volume 20 μl). After 1 hour incubation at 37° C., the aliquots were loaded on 1.5% agarose gel, run at 100 V for 3 to 4 hours, transferred onto a nylon membrane (Hybond N+, Amersham), and analyzed with a PhosphorImager. For more details, see (21).

Caspase activity. VSMC-E1A seeded in 20 cm$^2$ flasks and treated as indicated in FIG. 5 were scratched, transferred to centrifuge tubes, washed twice with PBS and lysed in 0.5 ml of buffer A contaming 50 mM tris-HCl (pH 7.4), 5 mM MgCl$_2$, 1 mM EGTA and 0.1% CHAPS. Then, 50–100 μl of cell lysate was mixed with 600 μl of buffer A containing 1 mM dithiothreitol, 40 μM YVAD-AMC or DEVD-AMC with or without 1 μM of caspase-1 and capspase-3 inhibitors (Ac-YVAD-CHO and Ac-DEVD-CHO, respectively), incubated for 2 hours at 37° C. and diluted 15-fold with 80 mM glycine-NaOH buffer (pH 10). Fluorescence of the samples was measured at $_{ex}$=365 run and $_{em}$=465 run and calibrated with AMC in the range of 10 to 100 nM. To measure caspase activity in control and ouabain-treated Jurkat cells, 5 ml of suspension containing ~2×10$^7$ cells was transferred onto ice and sedimented. The pellet of cells was washed and treated with 0.3 ml of medium A in the same way as VSMC. Protein content was estimated by Bradford methods.

Intracellular Na$^+$ and K$^+$ content. The intracellular content of exchangeable Na$^+$ and K$^+$ was measured as steady-state distribution of extra- and intracellular $^{22}$Na and $^{86}$Rb, as described previously in detail (22). Briefly, to establish the steady-state distribution of isotopes, VSMC growing in 12× ($^{22}$Na) or 24× ($^{86}$Rb) well plates or ~10$^6$ Jurkat cells in suspension were preincubated for 24 hours in DMEM containing 10% calf serum and 0.5 μCi/ml $^{86}$RbCl or 2 μCi/ml $^{22}$NaCl and then treated in media with compositions shown in FIG. 1 and Tables 3 and 4 and with the same specific radioactivity. At the end of incubation, the VSMC were transferred on ice, washed 4 times with 2 ml of ice-cold medium W, containing 100 mM MgCl$_2$ and 10 mM HEPES-tris buffer (pH 7.4), and lysed with SDS/EDTA mixture. One ml of Jurkat cell suspension was applied on a Whatman type C filter with the cells being washed with 3×5 ml aliquots of ice-cold medium W under negative pressure of 20–30 mm Hg. Radioactivity of the incubation medium and cell lysate was measured with a liquid scintillation analyzer and intracellular cation content was determined as A/am, where A was the radioactivity of the samples (cpm), a was the specific radioactivity of Na$^+$ and K$^+$($^{86}$Rb) in the medium (cpm/nmol), and m was the protein content determined by Lowry methods.

References

1. Wyllie, A. H. (1981) in *Cell death in biology and pathology* (Bowen, I. D. and Lockshin, R. A. eds) pp. 9–34, Chapman and Hall, London
2. Cotter, T. G., Lennon, S. V., Glynn, J. G., and Martin, S. J. (1990) *Cancer Res.* 10, 1153–1160
3. Prasad, C. V., Greer, W. L., Severini, A., and Kaplan, J. G. (1987) *Cancer Res.* 47, 5397–5400
4. Lubin, M. (1967) *Nature* 213, 451–453
5. Kaplan, J. G. (1978) *Ann. Rev. Physiol.* 40, 19–41
6. Lubin, M. (1980) *Biochem. Biophys. Res. Commun.* 97, 1060–1067
7. Brodie, C., Tordai, A., Saloga, J., Domenico, J., and Gelfand, E. W. (1995) *J Cell. Physiol.* 165, 246–253
8. Henningsen, N., Stavenow, L., and Borg, C. (1984) *Scand. J Clin. Lab. Invest.* 44, 197–201
9. Bobik, A., Grooms, A., Grinpukel, S., and Little, P. J. (1988) *J. Hypertens.* 6 (suppl.4), S219–221
10. Orlov, S. N., Dam, T. V., Tremblay, J., and Hamet, P. (1996) *Biochem. Biophys. Res. Commun.* 221, 708–715
11. Kerr, J. F. R., Wyllie, A. H., and Currie, A. R. (1972) *Br. J. Cancer* 26, 239–257
12. Ohyama, H., Yamada, T., and Watanabe, I. (1981) *Radiat. Res.* 85, 333–339
13. Klassen, N. V., Walker, P. R., Ross, C. K., Cygler, J., and Lach, B. (1993) *Int. J. Radiat. Biol.* 64, 571–581
14. Bortner, C. D., Hughes, F. M., and Cidlowski, J. A. (1997) *J. Biol. Chem.* 272, 32436–32442
15. Lang, F., Madlung, J., Uhlemann, A. C., Risler, T., and Gulbins, E. (1998) *Pflugers Archiv* 436, 377–383

16. Lang, F., Lepple-Wienhues, A., Szabo, I., Siemen, D., and Gulbins, E. (1998) in *Cell Volume Regulation. Contrib. Nephrol.* (Lang, F. ed) pp. 158–168, Karger, Basel
17. Franks, D. J., Plamondon, J., and Hamet, P. (1984) *J. Cell. Physiol.* 119, 41–45
18. Bennett, M. R., Evan, G. I., and Newby, A. C. (1994) *Circ. Res.* 74, 525–536
19. Bennett, M. R., Evan, G. I., and Schwartz, S. M. (1995) *Circ. Res.* 77, 266–273
20. Gamer, R., Helgason, C. D., Atkinson, E. A., Pinkoski, M. J., Ostergaard, H. L., Sorensen, O., Fu, A., Lapchak, P. H., Rabinovitch, A., McElhaney, J. E., Berke, G., and Bleackley, R. C. (1994) *J. Immunol.* 153, 5413–5420
21. Hamet, P., Richard, L., Dam, T. V., Teiger, E., Orlov, S. N., Gaboury, L., Gossard, F., and Tremblay, J. (1995) *Hypertension* 26, 642–648
22. Orlov, S. N., Tremblay, J., and Hamet, P. (1996) *J. Membrane Biol.* 153, 125–135
23. Webb, G. D., Taylor, E. A., Oh, V. M. S., Yeo, S.-B., and Ng, L. L. (1995) *Clin. Sci.* 88, 695–700
24. Champagne, M.-J., Dumas, P., Orlov, S. N., Bennett, M. R., Hamet, P., and Tremblay, J. (1999) *Hypertension* (in press)
25. Widmann, C., Gibson, S., and Johnson, G. L. (1998) *J. Biol. Chem.* 273, 7141–7147
26. Bertrand, R., Solary, E., O'Connor, P., Kohn, K. W. and Pommier, Y. (1994) *Exp. Cell Res.* 211, 314–321
27. Bortner, C. D. and Cidlowski, J. A. (1996) *Am. J. Physiol.* 271, C950–C961
28. Janicke, R. U., Sprengart, M. L., Wati, M. R., and Porter, A. G. (1998) *J. Biol. Chem.* 273, 9357–9360
29. Thornberry, N. A. and Lazebnik, Y. (1998) *Science* 281, 1312–1316
30. Nicholson, D. W., All, A., Thornberry, N. A., Vaillancourt, J. P., Ding, C. K., Gallant, M., Gareau, Y., Griffin, P. R., Labelle, M., Munday, N. A., Raju, S. M., Smulson, M. E., Yamin, T. T., Yu, V. L., and Miller, D. K. (1995) *Nature* 376, 37–43
31. Hughes, F. M., Bother, C. D., Purdy, G. D., and Cidlowski, J. A. (1998) *J. Biol. Chem.* 272, 30567–30576
32. Olej, B., dos Santos, N. F., Leal, L., and Rumjanek, V. M. (1998) *Biosci. Rep.* 18, 1–7
33. Balasubramanyam, M., Rohowsky-Kochan, C., Reeves, J. P., and Gardner, J. P. (1994) *J. Clin. Invest.* 94, 2002–2008
34. Berthe, P., Cousin, J. L., and Breittmayer, J. P. (1991) *Cellular Signalling* 3, 453–459
35. Oshiri, Y. and Miyazaki, S. (1995) *J. Immunol.* 154, 599–609
36. McConkey, D. J. and Orrenius, S. (1997) *Biochem. Biophys. Res. Commun.* 239, 357–366
37. Orlov, S. N., DeBlois, D., Tremblay, J., and Hamet, P. (1999) *Cardiovasc. Risk Factors* (in press)
38. Rosette, C. and Karin, M. (1996) *Science* 274, 1194–1197
39. Geng, Y.-J., Henderson, L. E., Levesque, E. B., Muszynski, M., and Libby, P. (1997) *Arterioscler. Thromb. Vasc. Biol.* 17, 2200–2208
40. Bennett, M. R., Macdonald, K., Chan, S.-W., Luzio, J. P., Simari, R., and Weissberg, P. (1998) *Science* 282, 290–293
41. Green, D. R. (1998) *Cell* 94, 695–698
42. Adachi, S., Gottlieb, R. A., and Babior, B. M. (1998) *J. Biol. Chem.* 273, 19892–19894
43. Luo, X., Buihardjo, I., Zou, H., Slaughter, C., and Wang, X. (1998) *Cell* 94, 481–490
44. Bossy-Wetzel, E., Newmeyer, D. D., and Green, D. R. (1998) *EMBO J* 17, 37–49
45. Hakem, R., Hakem, A., Duncan, G. S., Henderson, J. T., Woo, M., Soengas, M. S., Elia, A., de la Pompa, J. L., Kagi, D., Khoo, W., Potter, J., Yoshida, R., Kaufman, S. A., Lowe, S. W., Penninger, J. M., and Mak, T. W. (1998) *Cell* 94, 339–352

What is claimed is:

1. A method for inhibiting apoptosis in a vascular smooth muscle cell (VSMC) or for increasing a vascular smooth muscle cell's resistance to apoptosis, comprising increasing the vascular smooth muscle cell's intracellular $[Na^+]/[K^+]$ ratio, wherein said increasing the vascular smooth muscle cell's intracellular $[Na^+]/[K^+]$ ratio inhibits apoptosis in a VSMC or increases a vascular smooth muscle cell's resistance to apoptosis.

2. The method of claim 1, wherein said intracellular $[Na^+]/[K^+]$ ratio is increased by inhibiting $Na^+/K^+$ pump activity.

3. The method of claim 1, wherein said intracellular $[Na^+]/[K^+]$ ratio is increased by increasing the cell's intracellular $Na^+$ content.

4. The method of claim 1, which inhibits the cell's caspase-3 biological activity.

5. The method of claim 1, which blocks the cells induced chromatin cleavage.

6. The method of claim 1, which prevents the cell's DNA laddering.

7. The method of claim 1, comprising the step of contacting said cell with a compound selected from the group consisting of Ouabain, Digoxin (Digoxigenin), Digitoxin (Digitoxigenin), Acetyldigoxin, Acetyldigitoxin, Gitaloxin (Gitoxigenin), Deslanosid, Lanatosid C, Ouabagenin, Scillaren, Strophantin, Proscillaridin, Thevetosid, Bufanin, and Bufadienolid.

8. The method of claim 7, comprising the step of contacting said cell with a compound selected from the group consisting of Ouabain, Digoxin (Digoxigenin) and Digitoxin (Digitoxigenin).

9. A method for inhibiting caspase-3 biological activity in a vascular smooth muscle cell (VSMC), comprising increasing the vascular smooth muscle cell's intracellular $[Na^+]/[K^+]$ ratio, wherein said increasing the vascular smooth muscle cell's intracellular $[Na^+]/[K^+]$ ratio inhibits caspase-3 biological activity in a VSMC.

10. A method for blocking induced chromatin cleavage in a vascular smooth muscle cell (VSMC), comprising increasing the vascular smooth muscle cell's intracellular $[Na^+]/[K^+]$ ratio, wherein said increasing the vascular smooth muscle cell's intracellular $[Na^+]/[K^+]$ ratio blocks induced chromatin cleavage in a VSMC.

11. A method for preventing DNA laddering in a vascular smooth muscle cell (VSMC), comprising increasing the vascular smooth muscle cell's intracellular $[Na^+]/[K^+]$ ratio, wherein said increasing the vascular smooth muscle cell's intracellular $[Na^+]/[K^+]$ ratio prevents DNA laddering in a VSMC.

* * * * *